United States Patent [19]

Van Kruchten et al.

[11] Patent Number: 4,810,398

[45] Date of Patent: Mar. 7, 1989

[54] PREPARATION OF A BASIC SALT

[75] Inventors: Eugëne M. G. A. Van Kruchten; Rudolf R. Van Well, both of Amsterdam, Netherlands

[73] Assignee: Shell Oil Company, Houston, Tex.

[21] Appl. No.: 147,951

[22] Filed: Jan. 25, 1988

[30] Foreign Application Priority Data

Feb. 16, 1987 [GB] United Kingdom ............... 8703549

[51] Int. Cl.$^4$ ........................................ C10M 129/40
[52] U.S. Cl. ........................................ 252/40; 252/38; 252/32
[58] Field of Search .................... 252/38, 39, 40, 33.4

[56] References Cited

U.S. PATENT DOCUMENTS

| 3,567,637 | 3/1971 | Sabel | 252/39 |
| 4,597,880 | 7/1980 | Eliades | 252/33.4 |

FOREIGN PATENT DOCUMENTS

| 0208750 | 10/1956 | Australia | 252/39 |
| 786167 | 11/1957 | United Kingdom . | |
| 1146925 | 3/1969 | United Kingdom | 252/39 |
| 2097417 | 11/1982 | United Kingdom . | |

Primary Examiner—William R. Dixon, Jr.
Assistant Examiner—James M. Hunter, Jr.

[57] ABSTRACT

A basic alkaline earth metal salt of a blend of organic carboxylic acids is prepared by (a) preparing a mixture of one equivalent of the blend of organic carboxylic acids and more than one equivalent of an alkaline earth metal hydroxide and/or oxide in a hydrocarbon solvent;

(b) introducing carbon dioxide into the mixture obtained in an amount of at least 0.5 equivalent carbon dioxide per equivalent of excess alkaline earth metal; and (c) removing residual solids, if any, and an aqueous layer, if any, whereby the blend of organic carboxylic acids comprises a $C_{8-30}$ alkyl salicylic acid and one or more alkanecarboxylic acids in which the alkyl moiety is branched and has from 4 to 40 carbon atoms.

Such a salt has dispersant properties and is suitable for use in lubricating oil and fuel compositions.

22 Claims, No Drawings

PREPARATION OF A BASIC SALT

BACKGROUND OF THE INVENTION

1. Field of the Invention

The present invention relates to a process for the preparation of a basic alkaline earth metal salt of a blend of organic carboxylic acids, a salt thus prepared and to oil compositions containing such a salt.

2. State of the Art

The use of alkaline earth metal salts of organic carboxylic acids as additives for lubricating oil compositions is known. The said salts have a dispersant property so that they, when applied in such composition, ensure that the inside of engine cylinders remains clean and that deposition of carbonaceous products on pistons and in piston grooves is counteracted, so that piston-ring sticking is prevented.

It is also known to prepare basic (or overbased) alkaline earth metal salts of such acids. The overbasing provides an alkaline reserve which, when applied in lubricating oil compositions, reacts with and neutralises acidic compounds formed during the operation of the engine in which the composition is applied. Hence, sludge which may arise, is maintained dispersed due to the dispersant property of the salt while acids which would enhance sludge formation are neutralised.

In British patent specification No. 786,167, a process for the preparation of basic salts is described in which an organic acid is reacted with an excess of an alkaline earth metal oxide or hydroxide in an oil and subsequently carbon dioxide is passed through the reaction mixture to yield basic salts. As suitable acids are mentioned substituted or unsubstituted aliphatic, cycloaliphatic and aromatic acids, comprising carboxylic acids, sulphur-containing acids, phosphoric acids, thio-acids, phenols and partial esters of sulphur- and phosphorus-containing acids.

In the technical field there is a desire to use products with a basicity as high as possible, i.e. the relative proportion of the organic acid rest in the basic salt is as low as possible. The reason for this is that the costs of the product are mainly incurred by the costs of the organic acid.

The basicity of the products prepared according to the prior art process can amount up to a value of the basicity index of 10, the basicity index (BI) being defined as the equivalents ratio of the total of alkaline earth metal to the total of organic acids. It was found that in the preparation of products having such a high BI or an even higher BI using carboxylic acids a pronounced tendency to gelation occurs thereby severely hindering the handleability of the products. Another problem was that when using certain acids only relatively low BI values were obtainable. It has now been found that when a blend of two specific types of carboxylic acids is used, a high BI value can be obtained without incurring gelation problems.

SUMMARY OF THE INVENTION

Accordingly, the present invention relates to a process for the preparation of a basic alkaline earth metal salt of a blend of organic carboxylic acids, which comprises (a) preparing a mixture of one equivalent of the blend of organic carboxylic acids and more than one equivalent of an alkaline earth metal hydroxide and/or oxide in a hydrocarbon solvent;

(b) introducing carbon dioxide into the mixture obtained in an amount of at least 0.5 equivalent carbon dioxide per equivalent of excess alkaline earth metal; and (c) removing residual solids, if any, and an aqueous layer, if any, whereby the blend of organic carboxylic acids comprises a $C_{8-30}$ alkyl salicylic acid and one or more alkanecarboxylic acids in which the alkyl moiety is branched and has from 4 to 40 carbon atoms.

Particularly preferred are alkyl salicylic acids having at least 10 carbon atoms in the alkyl group, in particular from 12 to 26 carbon atoms.

The alkanecarboxylic acid used in the present invention is long enough to avoid any solubility problems in oil compositions such as lubricants, and it is not too long to incur problems in naphthenic or aromatic oil compositions. Preferably, the alkyl moiety has 8 to 28 carbon atoms.

The alkanecarboxylic acid is branched. It is even more preferred that the alkyl moiety is a tertiary alkyl moiety. The tertiary carboxylic acids are so suitable since when they are used very high BI values can be obtained. It is submitted that the total number of the tertiary alkyl group must not exceed 40. It appeared that the lengths of the branches of the branched alkyl group are not critical. It has little or no effect, when the total number of carbon atoms in the tertiary alkyl group is the same. Very suitable acids include mixtures of tertiary acids, like those traded under the trade name "VERSATIC" acids (ex Shell Nederland Chemie). These acids are prepared by subjecting an olefin, e.g. a propylene oligomer, or a linear olefin, like those sold under the trade name "SHOP" (ex Shell Chemicals UK) to a Koch reaction, yielding branched carboxylic acids. When mixtures of acids are used the preferred length of the alkyl moiety relates to the average length of the alkyl groups.

The ratios between the alkyl salicylic acid and the alkane carboxylic acid may vary within wide ranges. Advantageously the equivalent ratio of the alkyl salicyclic acid to alkanecarboxylic acid ranges from 10:1 to 1:10, preferably from 4:1 to 1:4.

The alkaline earth metal salts prepared include magnesium, calcium, strontium and barium salts. Preferably, the alkaline earth metal applied is magnesium or calcium.

The reaction mixture prepared in step (a) of the present process suitably further contains a promoter, preferably an oxygen-containing organic solvent and optionally water. Suitable solvents include $C_{1-6}$ alcohols, polyhydric alcohols such as glycol, propylene glycol, glycerol or 1,3-dihydroxypropane, ethers such as $C_{1-4}$ monoethers of glycol or propylene glycol, di isopropyl ether, 1,3- or 1,4-dioxane, or 1,3-dioxolane. Preferably the promoter is a $C_{1-6}$ alcohol, in particular methanol.

It will be appreciated that in industrial processes use may be made of technical solvents, and that the use of technically pure promoters, such as methanol, might incur the presence of water. Hence, in such cases addition of water per se is not required since its addition is made implicitly by the addition of the promoter.

The preparation of the mixture according to step (a) of the present process can be carried out at any possible way, e.g. by mixing the alkaline earth metal hydroxide and/or oxide with the promoter and adding the acids, whether or not in the presence of the promotor or the hydrocarbon solvent to the resulting mixture. It is preferred to mix the blend of the acids and the alkaline earth metal hydroxide and/or oxide in a hydrocarbon solvent and subsequently adding the promoter. The promotor may contain a substantial amount of water. Preferably the water content is adjusted such that the percentage of water in the mixture amounts to 0 to 10% w, based on the total liquids.

The hydrocarbon solvent can be selected from a wide variety of solvents. Suitable solvents include hydrocarbon oils, such as solvent-refined and/or hydrogenated lubricating oils having a kinematic viscosity of 3.5–35 $mm^2/s$ at 100° C. Preferably it is an aromatic hydrocarbon or a hydrocarbon fraction rich in aromatics, such as gasoline. Suitable hydrocarbon solvents are benzene, toluene, xylene or mixtures thereof, xylene being particularly preferred. The amount of the solvent is not critical. Promotor:solvent volume ratios up to 1 can suitably be applied, preference being given to ratios in the range from 0.1 to 0.6.

The concentration of the organic carboxylic acid in the solvent or solvent mixture can vary within wide limits. Suitably the equivalent concentration of acids is from 0.01 to 1 molar equivalent/kilogram, preferably from 0.1 to 0.8, based on the combined weight of organic carboxylic acids and hydrocarbon solvent.

The amount of alkaline earth metal to be added to step (a) should be at least 1 equivalent. Preferably the amount alkaline earth metal is more, so that the subsequent carbon dioxide supply results in very high BI compounds. Then, the amount of alkaline earth metal hydroxide and/or oxide added in step (a) is preferably from 10 to 25 equivalents per equivalent acid.

The temperature at which step (a) is carried out is not critical. It may be ambient temperature or elevated temperature. Suitable temperatures include 15°–150° C.

In step (b) the temperature is advantageously from 15° to 150° C., preferably from 30° to 75° C. In order to obtain the elevated temperature it may be necessary to employ elevated pressures, since the desired reaction temperature may be above the atmospheric reflux temperature of the reaction mixture. Suitable pressures include 1 to 15 bar abs. Higher pressures are possible, but merely add to the costs of the process. The rate at which the carbon dioxide is introduced is advantageously from 0.05 to 1.0 equivalent carbon dioxide per equivalent acid per minute. The carbon dioxide introduction is conveniently carried out by passing carbon dioxide, or a mixture of carbon dioxide with an inert gas, such as air or nitrogen, through the reaction mixture under slightly higher pressure than the pressure prevailing in the reaction mixture. Higher pressures may be employed. Carbon dioxide will be absorbed in the reaction mixture and will react with the alkaline earth metal compounds present therein forming a basic complex salt of the organic acid salt and carbonate, hydroxide and/or oxide. The amount of carbon dioxide to be taken up in step (b) is to a certain extent dependent on the amount of alkaline earth metal added in step (a) of the present process. Suitably the relative amount of carbon dioxide is somewhat less than the relative amount of alkaline earth metal hydroxide or oxide.

Preferably the introduction of carbon dioxide in step (b) is stopped after 0.5 to 0.9 equivalent carbon dioxide per equivalent alkaline earth metal has been taken up. Conveniently, this corresponds with 5 to 23 equivalent carbon dioxide per equivalent acid.

It has been found that an ageing period between step (b) and step (c) can be advantageous, since it increases the BI of the resulting basic salt. Such an ageing period amounts suitably to at least 15 min. A maximum period is generally imposed by practical and/or economical reasons, and is generally below 20 hours. Preferably the period between steps (b) and (c) is from 1 to 4 hrs.

The reaction mixture at the end of step (b) may be worked up by any method known in the art. It may be subjected to a centrifuging treatment to remove solids comprising unreacted alkaline earth metal hydroxide and/or oxide and/or non-colloidal alkaline earth metal carbonate, if any. The resulting solution may then be subjected to a liquid-phase separation. One liquid phase can be an aqueous layer which may contain the promoter when it is used, the other one is the hydrocarbon solvent plus the basic salts dispersed therein. It is also possible to reverse the above operations.

The present process can be used for the preparation of basic salts having a wide variety of basicity indices. So, it would be possible to prepare basic salts having a relatively low BI e.g. from 1 to 10. The present process, however, is excellently suitable for preparing basic salts having a basicity index from 10 to 20.

The process described is a one-step process. However, it is possible to integrate the process according to the present invention in a two-step process, such as in a two-step process according to British patent application No. 8613815. Thereto, step (a) and (b) of the present process are carried out in two stages, a1, a2, b1 and b2, respectively, whereby the stages comprise:

(a1) preparing a mixture of one equivalent of the blend of the organic carboxylic acids and more than one equivalent of an alkaline earth metal hydroxide and/or oxide in a hydrocarbon solvent;

(b1) introducing carbon dioxide into the mixture obtained until at least 0.5 equivalent carbon dioxide per equivalent of excess alkaline earth metal has been taken up;

(a2) adding at least one further equivalent of alkaline earth metal hydroxide and/or oxide to the reaction mixture, so that the total amount of alkaline earth metal hydroxide and/or oxide is at least 10 equivalent;

(b2) resuming the introduction of carbon dioxide to the resulting mixture.

Between stages (b1) and (a2) and after (b2) ageing periods can be employed as is indicated in the above patent application. The ageing period after stage (b2) corresponds with the above-mentioned ageing period between steps (b) and (c).

The process according to the present invention can be carried out batchwise and also in a continuous manner.

The basic salts are excellent dispersant additives in oils. Therefore the present invention also provides oil compositions comprising a major amount of a base oil and a minor amount of a basic alkaline earth metal salt as described hereinbefore. Preferably the base oil is a lubricating base oil.

The lubricating base oil in the composition according to the invention will conveniently constitute more than 50% w of the composition. It can be selected from mineral lubricating oils of varying viscosities, but it also includes a synthetic lubricant, such as ester-type lubricant or a polyolefin-type fluid, or a vegetable oil, or a grease.

Fuel compositions which are used in marine diesel engines usually contain some sulphur compounds. To neutralize the acidic compounds formed from these sulphur compounds a relatively high concentration of the basic salt is employed. Preferably, these marine lubricating oil compositions contain from 5 to 30% w of basic alkaline earth metal salt. Lubricating oil compositions for road engines may contain lower concentrations. The amount of basic alkaline earth metal salt in these lubricating oil compositions is preferably from 0.01 to 5% w, in particular from 0.1 to 4.0% w.

Fuels, such as gasoline, kerosine, diesel fuel and gas oils, can also contain the above basic salts. The amount of these salts is similar to that in road engine lubricating oil compositions or lower; conveniently the amount is from 0.001 to 5% w, in particular from 0.01 to 1.0% w.

The lubricating oil composition can be prepared by mixing a concentrate containing up to 60% w of a basic salt as described above in a lubricating oil, with a lubricating base oil to give the desired concentration. Such a concentrate is conveniently prepared by addition of a lubricating oil to the product obtained after completion of step (c), and removal of any volatile hydrocarbon solvent, water and alcohol, if present. The lubricating oil may be the same as the one indicated above as a suitable hydrocarbon solvent. The concentrate may conveniently contain a stabiliser, which is selected from a variety of organic compounds, such as those described in British patent specification No. 818,325. These compounds include mono-or polyhydric alcohols, alkyl amines and alkyl phenols.

The lubricating oil compositions may further contain a number of other additives, such as antioxidants, foam inhibitors, corrosion inhibitors, viscosity index improvers, and pour point depressants, as can be established by a person skilled in the art.

The invention will be illustrated by means of the following Examples.

EXAMPLE 1

The following experiments were carried to show the synergistic effect of using a blend of organic carboxylic acids in the process of the present invention.

COMPARATIVE EXAMPLE A 1340 ml of xylene was introduced together with 640 g of $C_{14}$-$C_{18}$ alkylsalicylic acid (ASA) (0.72 eq) and 400 g (10.8 eq) calcium hydroxide. The $Ca(OH)_2$/ASA ratio was 15:1. After stirring for 1 hour at 40° C. 390 ml methanol was added to the reaction mixture, and at 50° C. carbon dioxide was introduced at a rate of 0.12 eq $CO_2$/eq acid.min. After an uptake of 9.3 eq $CO_2$/eq acid the reaction mixture gelated to become a solid mass. A BI of this solid mass could not be determined, but in theory could only have reached a value of around 10–11.

COMPARATIVE EXPERIMENT B

A mixture of tertiary carboxylic acids, sold under the trade name "VERSATIC 10" was used in this experiment. The mixture (10) mainly consisted of 3-methyl-octane-3-carboxylic acid together with minor amounts of 4-methyl-octane-4-carboxylic acid, 3-ethyl-heptane-3-carboxylic acid and 4-ethyl-heptane-4-carboxylic acid. The acid number of this acids mixture was 5.8 meq/g. One equivalent of this mixture was added to xylene, yielding an acid concentration of 0.2 meq/g. Calcium hydroxide was added in an amount of 20 eq. After stirring for 1 hour methanol, 20% vol based on total liquid, was added to the reaction mixture at 44°–55° C. $CO_2$ was introduced at a rate of 0.40 eq $CO_2$/eq acid.min. After an uptake of 12 eq $CO_2$/eq acid the carbon dioxide stream was stopped. After settling of the two liquid phases now present, the methanol-water layer was removed. From the xylene layer the residual solids were removed by centrifugation. The BI of the calcium salt present in the xylene layer was 5.3.

EXPERIMENT 1

The procedure of comparative experiment B was repeated with a mixture of the ASA of experiment A and the V10 acids of experiment B. The relative amounts of the various reactants were 1 equivalent ASA per 1 equivalent V10 acid. The concentration of the acids in xylene was 0.4 meq $H^+$/g, and the relative amount of calcium hydroxide was 10 equivalent. Methanol, containing 3% vol water, was added in a quantity of 14.4% vol, based on the xylene. Carbon dioxide was introduced into the reaction mixture at a rate of 0.12 eq/eq acid.min at a temperature of 50°–55° C. After an $CO_2$ uptake of 7.1 eq/eq acid, the reaction mixture was worked up as described in experiment B, yielding a product having a BI of 8.8. No gelling was incurred.

EXPERIMENT 2

A two-steps process was carried out by following the procedure of Experiment 1 with the following amounts of reactants: ASA to V10 acids equivalents ratio is 7.3; the equivalent ratio of calcium hydroxide to acid is 10:1; the acid concentration, the composition of the solvents mixture, temperature and the $CO_2$ introduction rate were as described in Experiment 1. After a $CO_2$ uptake of 7.88 eq/eq acid, the reaction was interrupted for 15 minutes, calcium hyroxide was subsequently added in an amount of 7 eq/eq acid, the reaction mixture was stirred for one hour and the $CO_2$ introduction was resumed at 50° C. After a total uptake of 12.1 eq $CO_2$ (in both steps) the reaction mixture was treated as described in Experiment B, yielding a product with a BI of 14.8.

EXPERIMENT 3

The procedure of Experiment 2 was repeated. After the stopping of the $CO_2$ introduction at the second stage, i.e. after an uptake of 12.1 eq $CO_2$, the reaction mixture was subjected to an ageing period of 16 hours while stirring at 50° C. continued. After the work-up procedure as described in Experiment B a product with a BI of 15.1 was obtained.

From these experiments it is apparent that whereas the use of ASA or V10 acids alone yields unsatisfactory results, the use of a combination of these acids yield good products with a high BI and without incurring gelation problems. The use of an ageing period increases the BI of the product obtained.

EXAMPLE 2

In this Example a combination of ASA and tertiary carboxylic acids mainly having 19 carbon atoms (V19 acids) was used. The carboxylic acids have been prepared by subjecting $C_{18}$ alpha-olefins to a Koch reaction. The product of this reaction is a mixture of highly branched acids based on the $C_{18}$ olefin and its dimer which is formed during the reaction. The acid number of the mixture was 2.28 meq/g. Experiment 4 was carried out as a one step process as Experiment 1. Experiment 5 was carried out as Experiment 4 but with the use of a 16 hr ageing period as described in Experiment 3.

Experiments 6 and 7 were carried out as Experiment 3, i.e. with the use of a 16 hours ageing period.

The acids ratio, the $CO_2$-uptake in the various steps and the BI of the products obtained are indicated in Table 1 below.

TABLE 1

| Exp. No. | ASA/V19 (eq/eq) | $CO_2$ uptake (eq$CO_2$/eq acid) | | | BI product (eq/eq) |
|---|---|---|---|---|---|
| | | 1 step | 2 step | total | |
| 4 | 1:1 | — | — | 12.5 | 13.7 |
| 5 | 1:1 | — | — | 12.5 | 14.2 |
| 6 | 1:1 | 7.9 | 4.1 | 12.0 | 13.0 |
| 7 | 7:3 | 7.9 | 4.6 | 12.5 | 14.6 |

The product of Experiments 4–7 were introduced into a mineral lubricating oil, the mixtures obtained were subjected to vacuum distillation to remove xylene to yield concentrates. The calcium contents and the kinematic viscosities of the concentrates at 100° C. are indicated below.

TABLE 2

| Prod. of Exp. No. | Ca content % w | $V_k$ 100 (mm$^2$/s) |
|---|---|---|
| 4 | 10.1 | 15.1 |
| 5 | 10.1 | 12.7 |
| 6 | 9.7 | 10.2 |
| 7 | 9.8 | 14.3 |

EXAMPLE 3

The procedure of Experiment 2 was followed in the experiments 8 and 9. The differences between the latter experiments and Experiment 2 are as follows. The acids used in an equivalent ratio 1:1 were ASA and a mixture of tertiary carboxylic acids obtained as those described in Example 2 and having an acid number of 1.83 meq/g. In both steps an amount of calcium hydroxide of 12 eq/eq acid was added, i.e. the total calcium hydroxide amounted to 24 eq. In the work-up procedure residual solids were removed by filtration over a filter aid and not be centrifugation. Reaction conditions were as in Experiment 2. The $CO_2$ uptake and the BI's of the resulting products are given in Table 3.

TABLE 3

| Exp. No. | $CO_2$ uptake (eq$CO_2$/eq acid) | | | BI product (eq/eq) |
|---|---|---|---|---|
| | 1 step | 2 step | total | |
| 8 | 9.4 | 7.7 | 17.1 | 18.31 |
| 9 | 9.4 | 9.6 | 19.0 | 18.95 |

The products of these experiments were taken up in a lubricating oil as described in Example 2. The calcium contents and the kinematic viscosity are indicated below.

TABLE 4

| Prod. of Exp. No. | Ca content % w | $V_k$ 100 (mm$^2$/s) |
|---|---|---|
| 8 | 9.9 | 11.6 |
| 9 | 9.9 | 12.9 |

COMPARATIVE EXPERIMENT C

To show that linear carboxylic acids are not suitable for the present process a combination of stearic acid and ASA was used in a 1:1 equivalent ratio.

To 96.1 g of ASA and 32.0 g of stearic acid in 435.3 g of xylene 141.9 g of calcium hydroxide (17 eq/eq acid) was added together with 91.7 g of methanol and 2.8 g of water. This reaction mixture was subjected to a reaction as described under comparative Experiment B, and at a $CO_2$ uptake of 8.2 eq/eq acid the $CO_2$ introduction was interrupted due to severe gelation of the reaction mixture.

What is claimed is:

1. A process for the preparation of a basic alkaline earth metal salt of a blend of organic carboxylic acids, which comprises
   (a) preparing a mixture of one equivalent of the blend of organic carboxylic acids, which comprises a $C_{8-30}$ alkyl salicylic acid and one or more alkanecarboxylic acids in which the alkyl moiety is branched and has from 4 to 40 carbon atoms and more than one equivalent of an alkaline earth metal compound selected from the group consisting of hydroxides, oxides and mixtures thereof in a hydrocarbon solvent;
   (b) introducing carbon dioxide into the mixture obtained in an amount of at least 0.5 equivalent carbon dioxide per equivalent of excess alkaline earth metal; and
   (c) removing residual solids, if any, and an aqueous layer, if any.

2. A process according to claim 1, in which the alkyl salicylic acid has 12 to 26 carbon atoms in the alkyl group.

3. A process according to claim 2, in which the alkanecarboxylic acid has 8 to 28 carbon atoms in the alkyl moiety.

4. A process according to claim 1, in which the alkyl moiety of the alkanecarboxylic acid is a tertiary alkyl moiety.

5. A process according to claim 1, in which the equivalent ratio of the $C_{8-30}$ alkyl salicylic acid:alkanecarboxylic acid ranges from 10:1 to 1:10.

6. A process according to claim 5, in which the equivalent ratio of alkyl salicylic acid to alkanecarboxylic acid ranges from 4:1 to 1:4.

7. A process according to claim 1, in which the alkaline earth metal is calcium or magnesium.

8. A process according to claim 1, in which the mixture in step (a) further comprises an oxygen-containing organic solvent, optionally water.

9. A process according to claim 8, in which the oxygen-containing organic solvent is a $C_{1-6}$ alcohol.

10. A process according to claim 1, in which the mixture of the blend of the organic carboxylic acids and alkaline earth metal hydroxide compound is prepared by mixing the acids and the alkaline earth metal hydroxide and/or oxide in the hydrocarbon solvent.

11. A process according to claim 1, in which the hydrocarbon solvent is selected from the group consisting of benzene, toluene, xylene, or a mixture thereof.

12. A process according to claim 1, in which the amount of alkaline earth metal hydroxide compound added in step (a) is from 10 to 25 equivalents per equivalent acid.

13. A process according to claim 1, in which the introduction of carbon dioxide in step (b) is carried out at a temperature from 20° to 150° C.

14. A process according to claim 13, in which the temperature is from 30° to 75° C.

15. A process according to claim 1, in which the introduction of carbon dioxide in step (b) is carried out at a rate of 0.05 to 1.0 equivalent carbon dioxide per equivalent acid per minute.

16. A process according to claim 1, in which carbon dioxide is introduced in step (b) in an amount of 0.5 to 0.9 equivalent carbon dioxide per equivalent alkaline earth metal.

17. A process according to claim 1, in which the period between steps (b) and (c) is from 0.25 to 20 hours.

18. A process according to claim 1, wherein the alkyl salicylic acid has 12 to 26 carbon atoms in the alkyl group, the alkanecarboxylic acid has 8 to 28 carbon atoms in a tertiary alkyl group, the alkaline earth metal is selected from the group consisting of calcium or magnesium, the solvent is benzene, toluene, xylene or a mixture thereof.

19. A process according to claim 1, in which steps (a) and (b) are carried out in two stages, whereby the stages comprise:
(a1) preparing a mixture of one equivalent of the blend of organic carboxylic acids and more than one equivalent of an alkaline earth metal compound in a hydrocarbon solvent;
(b1) introducing carbon dioxide into the mixture obtained until at least 0.5 equivalent carbon dioxide per equivalent of excess alkaline earth metal has been taken up;
(a2) adding at least one further equivalent of alkaline earth metal hydroxide and/or oxide to the reaction mixture, so that the total amount of alkaline earth metal hydroxide and/or oxide is at least 10 equivalent;
(b2) resuming the introduction of carbon dioxide to the resulting mixture.

20. A process according to claim 19, wherein the alkyl salicylic acid has 12 to 26 carbon atoms in the alkyl group, the alkanecarboxylic acid has 8 to 28 carbon atoms in a tertiary alkyl group, the alkaline earth metal is calcium or magnesium, the solvent is selected from the group consisting of benzene, toluene, xylene and mixture thereof.

21. An oil composition comprising a major amount of a base oil and a minor amount of a basic alkaline earth metal salt prepared according to claim 1 effective as a dispersant.

22. A process according to claim 1, in which the mixture in step (a) further comprises an oxygen-containing organic solvent without water.

* * * * *